(12) United States Patent
Panian

(10) Patent No.: US 12,053,193 B2
(45) Date of Patent: Aug. 6, 2024

(54) ASPIRATION PUMP FOR REMOVAL OF FLUIDS, BLOOD CLOTS AND OTHER MATERIALS FROM HUMAN BODY

(71) Applicant: Anoxia Medical Inc., Hayward, CA (US)

(72) Inventor: Justin Panian, San Francisco, CA (US)

(73) Assignee: Anoxia Medical Inc., Hayward, CA (US)

( * ) Notice: Subject to any disclaimer, the term of this patent is extended or adjusted under 35 U.S.C. 154(b) by 0 days.

(21) Appl. No.: 18/510,399

(22) Filed: Nov. 15, 2023

(65) Prior Publication Data

US 2024/0081845 A1  Mar. 14, 2024

Related U.S. Application Data

(63) Continuation-in-part of application No. 17/964,695, filed on Oct. 12, 2022, which is a continuation of application No. 17/713,006, filed on Apr. 4, 2022, now Pat. No. 11,490,911, which is a continuation-in-part of application No. 17/384,203,
(Continued)

(51) Int. Cl.
| | |
|---|---|
| *A61M 1/00* | (2006.01) |
| *A61B 17/22* | (2006.01) |
| *A61M 25/00* | (2006.01) |
| *A61M 25/01* | (2006.01) |
| *A61M 39/06* | (2006.01) |
| *A61B 17/00* | (2006.01) |
| *A61B 90/00* | (2016.01) |

(52) U.S. Cl.
CPC ............... *A61B 17/22* (2013.01); *A61M 1/71* (2021.05); *A61M 1/84* (2021.05); *A61M 25/0012* (2013.01); *A61M 25/005* (2013.01); *A61M 25/0082* (2013.01); *A61M 25/0105* (2013.01); *A61M 39/06* (2013.01); *A61B 2017/00991* (2013.01); *A61B 2090/0811* (2016.02); *A61B 2090/3966* (2016.02); *A61M 1/60* (2021.05); *A61M 2210/0693* (2013.01); *A61M 2210/125* (2013.01); *A61M 2210/127* (2013.01)

(58) Field of Classification Search
CPC .......... A61M 1/74; A61M 1/743; A61M 1/85; A61M 1/90; A61M 2205/3569; A61M 2210/101; A61M 1/60; A61M 1/71; A61M 1/75; A61M 1/82; A61M 1/84; A61M 2205/8206; A61M 2210/0693; A61M 2210/125; A61M 2210/127; A61M 25/0012; A61M 25/005; A61M 25/0082; A61M 25/0105; A61M 39/06; A61B 17/22; A61B 2017/00991; A61B 2090/0811; A61B 2090/3966
See application file for complete search history.

(56) References Cited

U.S. PATENT DOCUMENTS

| | | | | |
|---|---|---|---|---|
| 5,738,656 | A | * | 4/1998 | Wagner .................... A61M 1/85 604/28 |
| 2007/0078444 | A1 | * | 4/2007 | Larsson ................ A61M 1/743 604/540 |

(Continued)

*Primary Examiner* — Kai H Weng
(74) *Attorney, Agent, or Firm* — Raymond Sun

(57) ABSTRACT

A suction pump system for aspirating fluids and other materials from a human body comprises a power source, an aspiration pump, and an electrical motor coupled to the power source and the aspiration pump, wherein the aspiration pump is pulsed at a frequency below 100 Hz.

18 Claims, 3 Drawing Sheets

Related U.S. Application Data filed on Jul. 23, 2021, now Pat. No. 11,890,024, which is a continuation of application No. 16/413,935, filed on May 16, 2019, now Pat. No. 11,096,703, which is a continuation-in-part of application No. 15/587,142, filed on May 4, 2017, now abandoned.

(56) References Cited

U.S. PATENT DOCUMENTS

| | | | |
|---|---|---|---|
| 2007/0219532 A1* | 9/2007 | Karpowicz | A61M 1/96 604/540 |
| 2013/0218106 A1* | 8/2013 | Coston | A61M 1/83 604/317 |
| 2016/0220741 A1* | 8/2016 | Garrison | A61M 25/0054 |
| 2019/0307985 A1* | 10/2019 | Panian | A61B 17/22 |
| 2022/0061870 A1* | 3/2022 | Mintz | A61B 17/22031 |

* cited by examiner

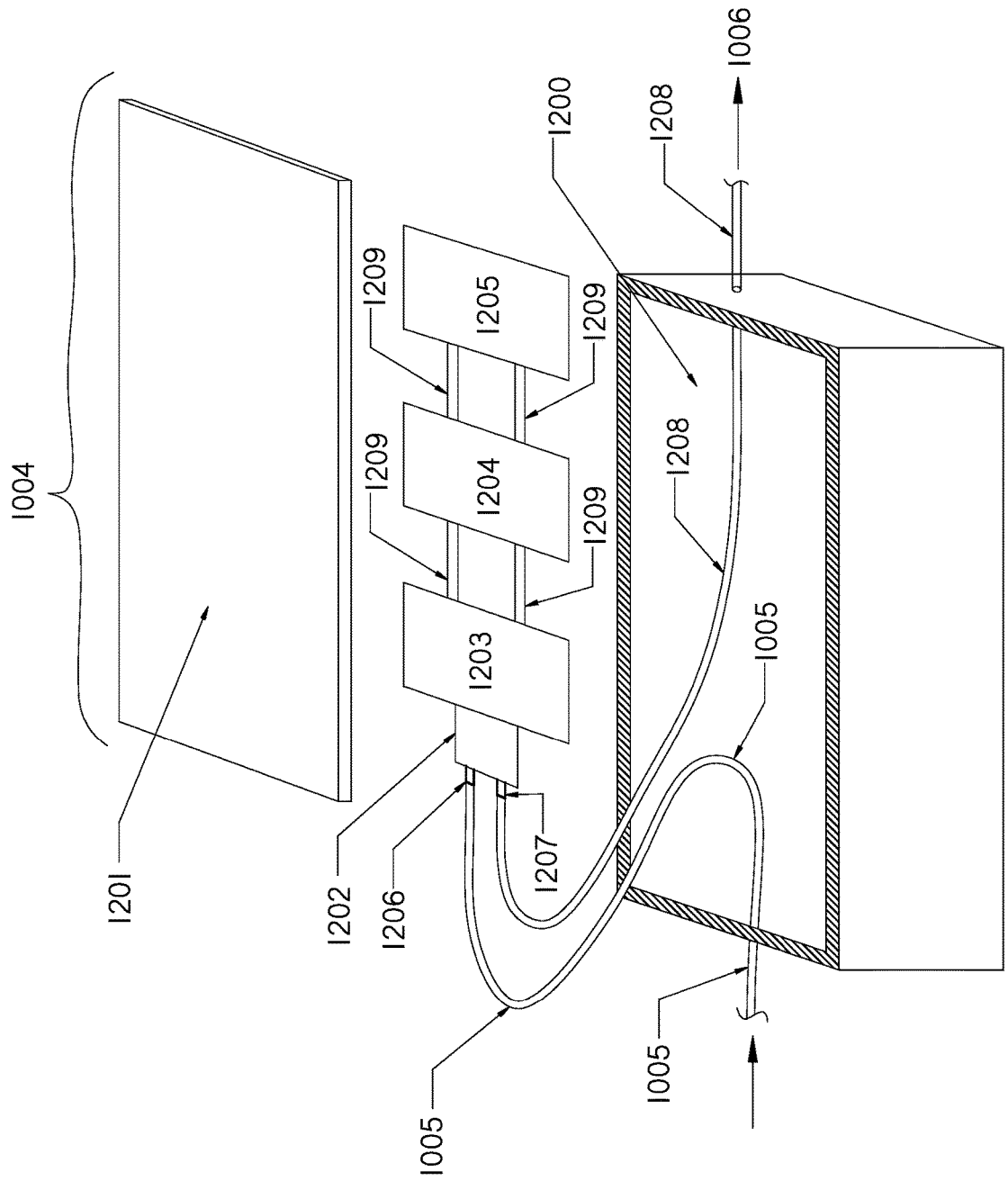

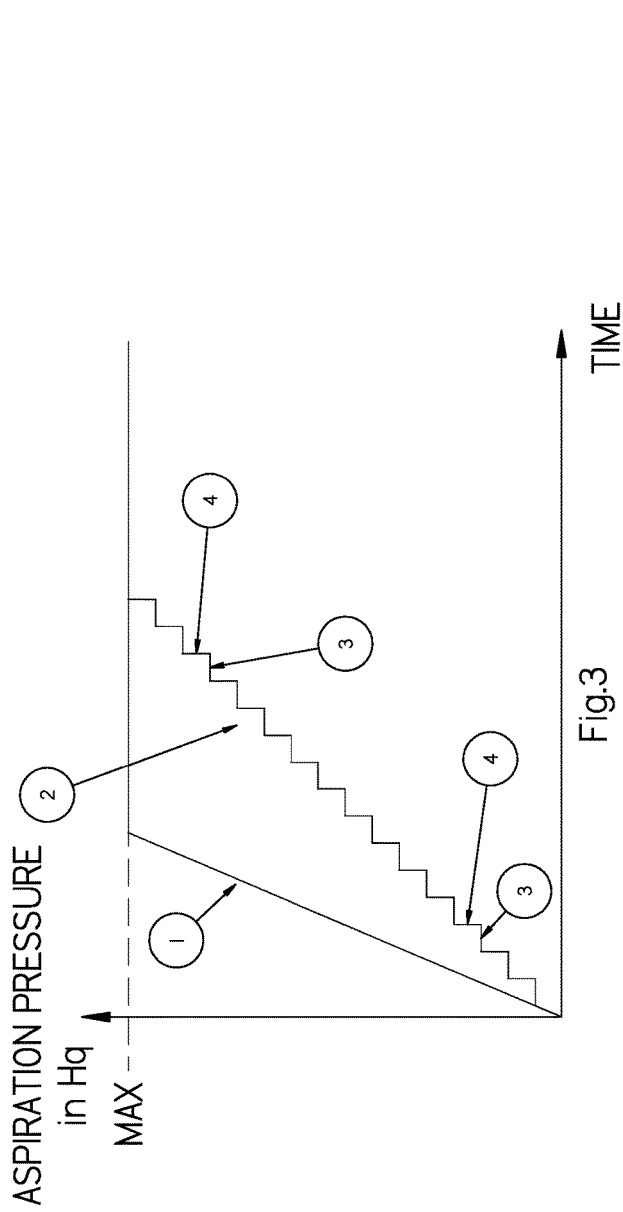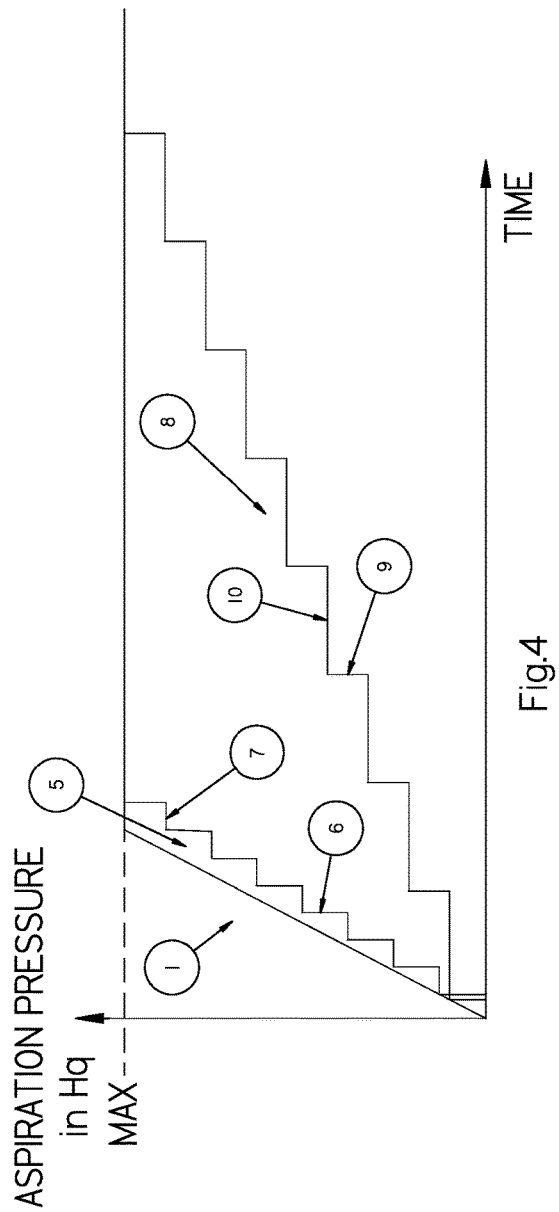

ASPIRATION PUMP FOR REMOVAL OF FLUIDS, BLOOD CLOTS AND OTHER MATERIALS FROM HUMAN BODY

BACKGROUND OF THE INVENTION

Field of the Invention

The present invention relates to methods and devices for removing thromboembolic materials and other tissue from human body.

Description of the Prior Art

Aspiration pumps have been generally used to remove fluids and other materials from the human body including but not limited to blood, saline, tissue, blood clots, plaque, food or for draining wounds. Endovascular catheters have been commonly used to remove fluids and other materials including thromboembolic blockages and other tissue from endovascular and non-endovascular locations in the human body. Single-lumen catheters are employed to aspirate a clot from a cerebral vessel, coronary vessels, and peripheral vessels. Such procedure in most cases includes placing a distal end/tip of a catheter at the proximal face of the clot and applying vacuum to the clot via a proximal port of the catheter. Fresh and soft clot usually are easily aspirated, while harder, more organized clot tends to clog the catheter. In such cases, the catheter with trapped clot and under suction is removed outside the patient. Then, the removed catheter is cleaned and introduced again to the treatment location to continue the clot removal process if necessary. However, in some cases, the clot is broken up in pieces by mechanical means during catheter removal and multiple introductions, causing a distal embolization and often dangerous clinical complications.

The latest development of aspiration devices has significantly improved recanalization rates. A direct aspiration, the ADAPT technique for stroke thrombectomy, was recently shown to be an effective and rapid way to achieve cerebral revascularization. This technique focuses on engaging and removing a clot without the use of ancillary devices and solely relying on aspiration forces generated by the suction pump through the catheter. While the use of aspiration alone to remove blood clots has significantly improved in the last several years, a single pass/use success rate still remains below 75%. Therefore, there is a need for better aspiration devices which are simple to use and which can quickly and safely remove fluids, particles, tissue fragments or thromboembolic pumps may further improve material.

SUMMARY OF THE DISCLOSURE

There are three approaches to improve the efficacy of removing blood clots using aspiration with a single lumen aspiration catheter: use of improved vacuum pumps to aid in aspiration of the clot through the catheter, use of larger aspiration catheters; and use of aspiration catheters with expandable tips.

Currently used air aspiration pumps are reaching almost an absolute vacuum of approximately 29.5 in-Hg (>14 psi) while aspirating air from a blood collection container with a maximum liquid negative pressure of also around 29.5 inHg. Also, use of pulsing aspiration pumps may increase aspiration efficacy. Another option is to increase the size (e.g., inner lumen) of the aspiration catheters. Increasing the size of the inner lumen of an aspiration catheter while maintaining the same diameter for the outer lumen is challenging because this compromises the required performance characteristics for the catheter, such as, for example, kink resistance. Use of innovative reinforcement may be helpful. Other options include the use of a catheter with a larger frontal aperture.

The present invention provides another option to increase efficacy of clot removal by pulsing aspiration pumps up and down, or on/off, to further disintegrate aspirated clot entering the aspiration catheter, thereby increasing the flow and volume of removed clots. In this regard, the present invention provides an aspiration system for aspirating blood clots from a human body, comprising a power source, an aspiration pump, and an electrical motor coupled to the power source and the aspiration pump, wherein the aspiration pump is pulsed at suitable frequency to increase removal efficacy of materials to be removed.

The following terms "aspiration", "vacuum" and "suction" are commonly used in this application, and all are related to using negative pressure that generally pertains to the movement of blood clots and other tissue caused by negative pressure.

The following terms "endovascular catheter", "aspiration catheter" and "catheter" have the same functional meaning, and all may be related to the removal of plaque, tissue, blood clots, blood and other liquids from the human body, as well as being used to deliver medications, implants, therapeutic agents and other matters.

As used herein, "treatment site" refers to any location in the body that has been or is to be treated by methods or devices of the present invention. Although "treatment site" often refers to an endovascular area including arteries and veins, the treatment site is not limited to endovascular tissue or blood clots. The treatment site may include tissues and blood clots associated with outside an endovascular location, including but not limited to bodily lumens, organs, ducts or localized tumors.

The treatment sites of the present invention involve blood vessels in the patient's vasculature, including veins, arteries, aorta, heart valves and particularly including cerebral, coronary and peripheral arteries and veins, as well as previously implanted grafts, shunts, fistulas and the like. In alternative embodiments, methods and devices to remove blood clots and other tissue described herein may also be applied, but are not limited to, the biliary duct, head, nerves, glands, and the like.

The scope of the present invention is best defined by drawings, descriptions below and the appended claims. In certain instances, descriptions of vacuum physics, well-known devices, compositions, components, mechanisms and methods are omitted so as to not obscure the description of the present invention with unnecessary details.

Some theoretical consideration and lab testing data have been introduced in the present invention for assessing and exploring how these therapeutic methods are effective. These considerations have been provided only for presenting an understanding of the invention only and do not limit the scope of the claims.

BRIEF DESCRIPTION OF THE DRAWINGS

FIG. 2 shows the details of the pump assembly of the aspiration system shown in FIG. 1.

FIG. 3 is a graph showing continuous aspiration pressure versus step-up aspiration pulsed at the same ON/OFF time.

FIG. 4 is a graph showing continuous aspiration pressure versus step-up aspiration pulsed at different ON/OFF times.

DETAILED DESCRIPTION OF THE PREFERRED EMBODIMENTS

Figure 1:
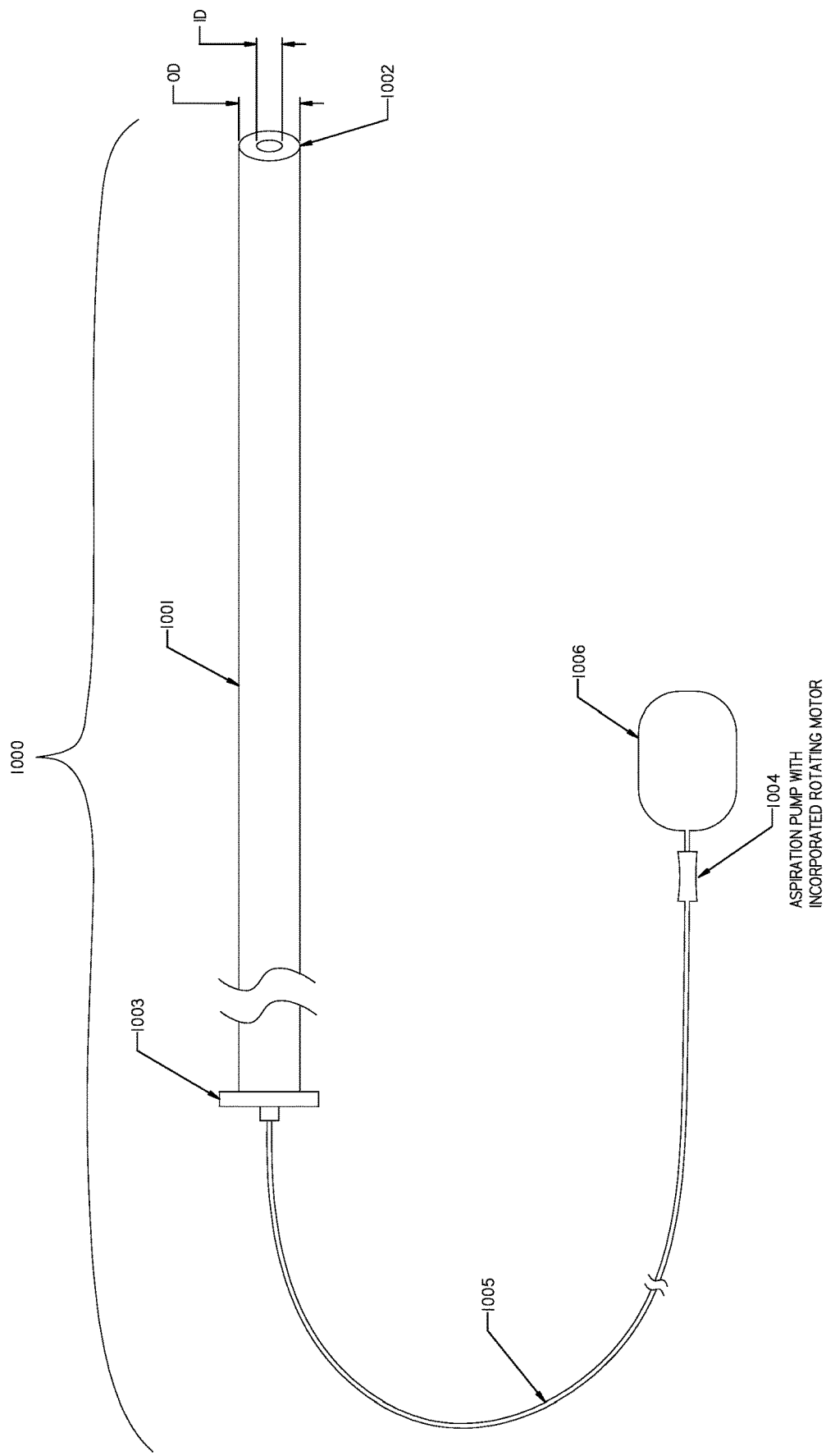
FIG. 1 shows an aspiration system for removing blood clots.

FIG. 1 shows a pulsing aspiration system 1000 including an aspiration catheter 1001 having a distal end 1002 and a proximal end 1003; and a liquid aspiration pump assembly 1004 attached via a tube 1005 to the proximal end 1003 of the aspiration catheter 1001. The liquid aspiration pump assembly 1004 is attached to a blood collection bag 1006. The liquid aspiration pump assembly 1004 functions to directly remove blood clots and other tissue from the body, unlike commonly-used air aspiration pumps that use air suction from inside the blood container to aspirate clots and other tissue. Pulsing of the liquid aspiration pump assembly 1004 may further enhance clot-removal efficacy. Higher clot recanalization rates may be achieved by pulsing aspiration, which in experimental work has outperformed static aspiration when liquid medium is used to aspirate synthetic clots. Such a trend may also indicate that higher recanalization rates may be achieved by pulsing aspiration of blood clots and other material to be removed from human body.

To secure maximum clot removal efficacy, the aspiration catheter 1001 should have the largest inner diameter and a thin wall to be compliant with the limiting inner diameters of introducer sheaths and guiding catheters that are commonly used in most interventional procedures. However, to secure catheter performance characteristics and compatibility with introducer sheaths and guiding catheters, it is advantageous that the ratio R of the catheter inner lumen diameter ID to the catheter outer lumen diameter OD should be more than 0.80.

The liquid aspiration pump assembly 1004 has mechanically actuated positive displacement powered by a rotating motor incorporated in the pump assembly as shown in FIG. 1 and may be powered by line power or battery. It is desirable to cycle the rotating motor and aspiration pump within 1-100 Hz frequency while maintaining the motor speed below 2000 RPM to achieve the best efficacy to remove clots and other liquids and tissue. Pulsing of the liquid aspiration pump assembly 1004 will cause the pump aspiration pressure to continuously change up and down, or on/off, and produce a pulsating effect on blood clots to be removed. Such blood clot pulsation will disrupt or break the structure of blood clots and prevent the aspiration catheter 1001 from clogging. The logic behind this approach is that pulsing pressure/forces will induce fatigue on the blood clots or other tissue to be removed, thereby enabling the removal of more entrenched blood clots and prevent catheter clogging.

FIG. 2 illustrates the aspiration pump assembly 1004 shown in FIG. 1. The liquid aspiration pump assembly 1004 includes an enclosure box having a bottom box 1200 and a top lid 1201, and a liquid diaphragm pump 1202 with actuated positive displacement that is activated by a rotating motor 1203. The motor 1203 which rotates the pump 1202, and the pump 1202, are coupled together and are powered by a battery 1204. The battery 1204 may be a single battery or a stack of batteries having output voltage between 6-24 VDC.

Between the battery 1204 and the motor 1203 there is a printed circuit board (PCB) 1205. The PCB 1205 functions to convert continuous voltage from the battery 1204 into pulsing voltage supplied to the motor 1203. The PCB 1205 may supply the motor 1203 with a pulsing voltage at a frequency between 1-100 Hz, and preferably 6-20 Hz. Motor 1203 receives pulsing voltage from the PCB 1205 and powers the pump 1202 with the same pulsing frequency, causing the pump 1202 to operate in a pulsing mode at the same frequency. Accordingly, the pump 1202 is operating in a pulsing on/off mode of operation at the frequency provided by the PCB 1205. The PCB 1205 is electrically attached to the battery 1204 and to the motor 1203 via electrical wires 1209.

The inlet 1206 of the pump 1202 is attached via the tube 1005 to the catheter 1001 as shown in FIG. 1. The outlet 1207 of the pump 1202 is attached to a tube 1208 that is further attached to the blood collection bag 1006 as shown in FIG. 1.

The motor 1203 can be any conventional motor that is used for similar applications, and is powered via the PCB 1205 by a single battery or a stack of batteries at 6-24 VDC. Also, the motor 1203 may be powered by a wall AC line converted to DC voltage, pulsed within 1-100 Hz frequency and further delivered to the motor 1203.

The aspiration pump assembly 1004 creates a maximum vacuum pressure up to 29.5 inHg instantaneously. Diaphragm liquid aspiration pump 1202 uses a combination of the reciprocating action of a rubber or thermoplastic diaphragm, and suitable shut-off valves on either side of the diaphragm, to pump a fluid. The pump 1202 can be any conventional diaphragm liquid aspiration pump that is used for similar applications. The rotations of the motor 1203 are converted into vertical eccentric movement of the diaphragm of the pump 1202. The diaphragm is sealed with one side in the fluid to be pumped, and the other side in hydraulic fluid. The diaphragm of the pump 1202 is stretched and expanded, causing the volume of the chamber of the pump 1202 to increase and decrease. Thus, the pump 1202 aspirates clots into the inlet 1206, which flows through the pump 1202 to the outlet 1207, and further via the outlet tube 1208, to the clot collection bag 1006 as shown in FIG. 1. To maintain a high aspiration pressure, the pump assembly 1204, aspiration catheter 1001 and connecting tubes 1005 and 1208 require pre-use priming with saline before use in aspirating clots.

The battery 1204 is electrically attached to the electrical inlets of the PCB 1205 via electrical wires 1209, and the outlet of the PCB 1205 is electrically attached via electrical wires 1209 to the motor 1203. Pulsing the pump 1202 is achieved by pulsing DC output voltage of the battery 1204 using the PCB 1205, thereby pulsing the motor 1203 which powers the pump 1202. A DC pulsed voltage output from the PCB 1205 is provided to the motor 1203 which is pulsed on/off at a frequency from 1-100 Hz causing the pump 1202 to cycle at the same frequency.

To maintain a higher aspiration pressure, the aspiration pump assembly 1004 should work continuously during clot removal without turning it totally off and on to avoid having any particles from the clot or plaque being stuck within the valves of the pump 1202.

The most common approach to remove blood clots from the human endovascular system is aspiration that includes using a single lumen aspiration catheter and an aspiration pump. Due to the organized structure of blood clots, it is often difficult to aspirate such clots in one pass or one aspiration approach.

Frequently, the aspiration catheter gets clogged and is required to be removed, cleaned, and reintroduced to the clot location to continue clot aspiration. Such steps are time-consuming and clinically undesirable.

Pulsing aspiration by pulsing the aspiration pump may induce fatigue into aspirated clots, fracture molecular bonds, and change its compliance, thereby facilitating clot removal and preventing the clogging of the aspiration catheter. Since liquid aspiration pumps are filled with liquid to function properly, and connected with the aspiration catheter which is also filled with liquid (blood or saline), a pulsating aspiration pump may be beneficial to improve clots removal.

The efficacy of pulsing aspiration was evaluated using the pulsing aspiration system 1000 with adjustable pulsing frequency between 0-10 Hz, and synthetic polyurethane clots. A large volume of synthetic clots was placed in a container and submerged in water. The pulsing aspiration system 1000 was filled with water and its distal end was placed against synthetic clots. The following two modes of aspiration were performed. In the first mode, the aspiration pump assembly 1004 was activated for 5 seconds of continuous aspiration. In the second mode, the aspiration pump assembly 1004 was activated and pulsed at 1-10 Hz frequency at increases of 1 Hz. After each 5 seconds of aspiration, the aspiration catheter 1001 was removed from the synthetic clots. The aspirated volume of the synthetic clots was registered for each aspiration approach. After each synthetic clot aspiration, the aspiration catheter 1001 was removed, cleaned, and prepared for another aspiration. This experiment was repeated three times for each aspiration cycle and the average volume of aspirated synthetic clots was calculated.

The volume of aspirated synthetic clots during each of 5 seconds of aspiration was as follows: at continuous (i.e, 0 Hz) aspiration—0 ml; at 1 Hz pulsing aspiration—0 ml; at 2 Hz pulsing aspiration—0 ml; at 3 Hz pulsing aspiration—2 ml; at 4 Hz pulsing aspiration—7 ml; at 5 Hz pulsing aspiration—12 ml; at 6 Hz pulsing aspiration—20 ml; at ?Hz pulsing aspiration—14 ml; at 8 Hz pulsing aspiration—9 ml; at 9 Hz pulsing aspiration—5 ml; at 10 Hz pulsing aspiration—3 ml as shown in Table 1.

TABLE 1

| | Mode of aspiration (Hz) | | | | | | | | | | |
|---|---|---|---|---|---|---|---|---|---|---|---|
| | 0 | 1 | 2 | 3 | 4 | 5 | 6 | 7 | 8 | 9 | 10 |
| Volume of aspirated synthetic clots (ml) | 0 | 0 | 0 | 2 | 7 | 12 | 20 | 14 | 9 | 5 | 3 |

This experiment demonstrates that pulsing aspiration outperforms continuous aspiration when using tested synthetic clots. Synthetic clots used in the experiment do not represent human blood clots and its consistency/uniformity is hardly repeatable. However, it shows that pulsing aspiration creates additional quiver forces that may separate and break up synthetic clot structure and therefore, potentially improve the aspiration of human blood clots. While pulsing aspiration at 3-10 Hz provides an improved aspiration outcome using synthetic clots, human clot aspiration which have a different characteristics may benefit from pulsing within 1-100 Hz to improve clot removal efficiency.

The aspiration pump assembly 1004 that provides uni-direction vacuum suction flows for the removal of fluids and other materials from the human body is shown in FIG. 2. The motor 1203 is coupled to the power source 1204 and to the pump 1202. The power source 1204 provides a voltage to motor 1203. The rotations of the motor 1203 drive the diaphragm of the pump 1202 via an oscillating connecting rod (not shown). There is a PCB circuit 1205 between the power source 1204 and the motor 1203 that is pulsing on/off or up and down power provided to the motor 1203, causing the motor 1203 rotations to be pulsed on/off or up and down. The pulsing of the motor 1203 is conveyed to the diaphragm of the pump 1202 at the same pulsing as the pulsing of the motor 1203. There are two one-way internal valves (not shown) inside the pump 1202, one on the inlet side and one on the outlet side, which together allow for uni-direction flow through the pump preventing any backflow. Such uni-direction flow will cause the pump 1202 to increase aspiration pressure to up to 29.5 inHg ("maximum pressure") if the inlet of the pump 1202 is blocked, and no flow is going through the pump 1202. Once the inlet of the pump 1202 is clear and uni-direction flow continues, the pump's pressure will vary to support the removal of blood clots and other material.

FIG. 3 shows two graphs. Graph 1 represents a continuous suction when the power is supplied to the motor 1202 directly from the power source 1204. The pump 1202 reaches up to 29.5 inHg pressure in a linear manner. Graph 2 on FIG. 3 shows aspiration pressure increased in a step-up manner. Such step-up aspiration pressure growth or increase is achieved by pulsing up and down or on and off on the pump 1202 using the power source 1204, the motor 1203 and the PCB circuit 1205. Horizontal portions 3 of graph 2 represent no aspiration increase when the pump 1202 is off; in other words, no power is being supplied to the motor 1203 and to the pump 1202. Vertical portion 4 of graph 2 represents aspiration pressure increase when the pump 1202 is on, and power from the power source 1204 is being provided to the pump 1202. Pulsing power on/off or up and down may have the same amount of time ON and the same amount of time OFF as shown by horizontal portion 3 of graph 2 and vertical portion 4 of the graph 2.

FIG. 4 show 3 different graphs. Graph 1 is similar to graph 1 in FIG. 3 and represents a continuous suction. Graph 5 shows pulsing aspiration up and down or on/off where the ON time represented by vertical line 6 is longer than the OFF time represented by horizontal line 7. Graph 8 shows pulsing aspiration up and down where the ON time represented by the vertical line 9 is shorter than the OFF time represented by horizontal line 10.

Such step-up pulsing of aspiration pressure will cause aspiration pressure stops or discontinuations, or short stops of suction. On/off pulsing of the aspiration pressure may modify the compliance of material to be removed; thus, breaking clot mass or other material mass endurance and improving its removal efficacy. Pulsing aspiration pump pressure within a range of 1-100 Hz is desirable due to response frequency limitation of the diaphragm aspiration pump.

This invention has been described with reference to preferred embodiments and examples, those having ordinary skill in this art will recognize that changes may be made in form and detail without departing from the spirit and scope of the invention as found in the claims which follow.

What is claimed is:

1. A aspiration pump system that provides vacuum suction flows in one direction for removing fluids and materials from a human body comprising:
    a power source;
    a diaphragm aspiration pump having an inlet to aspirate fluids and other materials into the pump and an outlet to remove fluids and other materials from the pump; and
    an electrical motor coupled to the power source and to the pump; wherein the pump is a uni-directional flow pump, and wherein the power source is pulsed repeatedly on and off to cause step-up increase in suction pressure of the pump while suction pressure increases.

2. The pump system of claim 1, wherein step-up increase in suction pressure continues until the pump reaches a pressure of up to 29.5 inHg.

3. The pump system of claim 2, wherein the pump suction pressure continues to be at up to 29.5 inHg aspiration pressure if the inlet of the pump is blocked and there is no flow of fluids or other material through the pump.

4. The pump system of claim 2, wherein the pump pressure of up to 29.5 inHg fluctuates to sustain flow of material to be removed if the inlet of the pump is cleared, and fluids and other materials continue to flow into the pump and out of the pump.

5. The pump system of claim 1, wherein a voltage provided to the motor from the power source is pulsed on/off at a frequency between 1-100 Hz.

6. The pump system of claim 1, wherein the aspiration pressure of the pump is pulsed on/off at a frequency between 1-100 Hz.

7. The pump system of claim 1, wherein a voltage from the power source is pulsed by an electrical circuit.

8. The pump system of claim 1, wherein the power source is one of the following: a battery, line power or combination of both.

9. The pump system of claim 1, further including a collection bag attached to the outlet of the pump.

10. The pump system of claim 1, further including an aspiration tube connected to the inlet of the pump.

11. The pump system of claim 10, further including an aspiration catheter attached to the aspiration tube.

12. A method for removing fluids and materials from a human body comprising:
providing a pump system having:
a power source;
a diaphragm aspiration pump having an inlet to aspirate fluids and other materials into the pump and an outlet to remove fluids and other materials from the pump; and
an electrical motor coupled to the power source and to the pump; and
providing a voltage to the motor from the power source which is pulsed repeatedly on and off to cause a step-up increase in suction pressure while suction pressure increases.

13. The method of claim 12, wherein the step-up increase in suction pressure continues until the pump reaches up to 29.5 inHg aspiration pressure.

14. The method of claim 13, wherein the pump suction pressure continues to be at up to 29.5 inHg aspiration pressure if the inlet of the pump is blocked and there is no flow of fluids or other material through the pump.

15. The method of claim 13, wherein the 29.5 inHg aspiration pressure fluctuates if the inlet of the pump is cleared, and fluids and other materials continue to flow into the pump and out of the pump.

16. The method of claim 12, wherein fluids and materials that are removed from the human body include: blood, saline, blood clots, atherosclerotic plug, tissue, other debris, or combination of all.

17. The method of claim 12, wherein a voltage provided to the motor from the power source is pulsed on/off at a frequency between 1-100 Hz.

18. The method of claim 12, wherein the aspiration pressure of the pump is pulsed on/off at a frequency between 1-100 Hz.

* * * * *